US008456150B2

(12) United States Patent
Shih et al.

(10) Patent No.: US 8,456,150 B2
(45) Date of Patent: Jun. 4, 2013

(54) HAND-HELD PHASE-SHIFT DETECTOR FOR SENSOR APPLICATIONS

(75) Inventors: Wan Y. Shih, Bryn Mawr, PA (US); Wei-Heng Shih, Bryn Mawr, PA (US)

(73) Assignee: Drexel University, Philadelphia, PA (US)

( * ) Notice: Subject to any disclaimer, the term of this patent is extended or adjusted under 35 U.S.C. 154(b) by 269 days.

(21) Appl. No.: 12/524,876

(22) PCT Filed: Jan. 30, 2008

(86) PCT No.: PCT/US2008/052388

§ 371 (c)(1), (2), (4) Date: Jul. 29, 2009

(87) PCT Pub. No.: WO2008/109205

PCT Pub. Date: Sep. 12, 2008

(65) Prior Publication Data

US 2010/0007330 A1 Jan. 14, 2010

Related U.S. Application Data

(60) Provisional application No. 60/887,686, filed on Feb. 1, 2007.

(51) Int. Cl.
*G01R 25/00* (2006.01)

(52) U.S. Cl.
USPC .................................... 324/76.77; 324/76.11

(58) Field of Classification Search
USPC .......................................... 324/76.77, 76.11
See application file for complete search history.

(56) References Cited

U.S. PATENT DOCUMENTS

| | | | | |
|---|---|---|---|---|
| 3,205,464 | A | | 9/1965 | Schwartz |
| 4,302,694 | A | | 11/1981 | Fujishima et al. |
| 4,349,762 | A | | 9/1982 | Kitamura et al. |
| 4,363,993 | A | | 12/1982 | Nishigaki et al. |
| 4,528,502 | A | | 7/1985 | Rocha |
| 4,649,312 | A | | 3/1987 | Robin et al. |
| 4,802,371 | A | | 2/1989 | Calderara et al. |
| 4,806,034 | A | * | 2/1989 | Plummer ...................... 400/279 |
| 5,054,323 | A | | 10/1991 | Hubbard et al. |
| 5,313,535 | A | | 5/1994 | Williams |
| 5,334,835 | A | | 8/1994 | Nakayama et al. |
| 5,445,008 | A | | 8/1995 | Wachter et al. |

(Continued)

FOREIGN PATENT DOCUMENTS

| | | | |
|---|---|---|---|
| EP | 0631319 | A1 | 12/1994 |
| EP | 1536227 | A2 | 6/2005 |

(Continued)

OTHER PUBLICATIONS

Wellman, P. S. et al., "Tactile Imaging: A Method for Documenting Breast Lumps", Feb. 2001.

(Continued)

*Primary Examiner* — Vincent Q Nguyen

(74) *Attorney, Agent, or Firm* — Mendelsohn, Drucker & Associates, P.C.

(57) ABSTRACT

The invention is directed to a novel phase-shift detector capable of interfacing with an array of sensors. The detector is light-weight, portable and capable of fitting within the palm of a hand. The detector may be used in conjunction with a variety of diagnostic, biosensor and chemical sensor applications.

20 Claims, 5 Drawing Sheets

1 Phase Shift Detector

U.S. PATENT DOCUMENTS

| | | | | |
|---|---|---|---|---|
| 5,475,318 | A | 12/1995 | Marcus et al. | |
| 5,503,010 | A | 4/1996 | Yamanaka | |
| 5,553,486 | A | 9/1996 | Bonin | |
| 5,689,063 | A | 11/1997 | Fujiu et al. | |
| 5,719,324 | A | 2/1998 | Thundat et al. | |
| 5,763,283 | A | 6/1998 | Cernosek et al. | |
| 5,780,727 | A | 7/1998 | Gimzewski et al. | |
| 5,807,758 | A | 9/1998 | Lee et al. | |
| 5,866,807 | A | 2/1999 | Elings et al. | |
| 5,874,126 | A | 2/1999 | Kahn et al. | |
| 5,909,129 | A * | 6/1999 | Murphy | 327/3 |
| 5,948,993 | A | 9/1999 | Ting et al. | |
| 5,966,787 | A | 10/1999 | Nakayama et al. | |
| 5,996,412 | A | 12/1999 | Hansen | |
| 6,075,585 | A | 6/2000 | Minne et al. | |
| 6,278,379 | B1 | 8/2001 | Allen et al. | |
| 6,280,396 | B1 | 8/2001 | Clark | |
| 6,289,717 | B1 | 9/2001 | Thundat et al. | |
| 6,336,366 | B1 | 1/2002 | Thundat et al. | |
| 6,422,069 | B1 | 7/2002 | Shimizu et al. | |
| 6,458,327 | B1 | 10/2002 | Vossmeyer et al. | |
| 6,465,368 | B2 | 10/2002 | Inoue et al. | |
| 6,589,727 | B1 | 7/2003 | Klenerman et al. | |
| 6,621,080 | B2 | 9/2003 | Yamamoto | |
| 6,734,425 | B2 | 5/2004 | Hantschel et al. | |
| 6,763,705 | B1 * | 7/2004 | Thundat et al. | 73/64.53 |
| 6,781,285 | B1 | 8/2004 | Lazarus et al. | |
| 6,823,720 | B1 | 11/2004 | Adkins et al. | |
| 6,903,491 | B2 | 6/2005 | Irie et al. | |
| 6,906,450 | B2 * | 6/2005 | Tamayo De Miguel et al. | 310/317 |
| 6,955,787 | B1 | 10/2005 | Hanson | |
| 6,992,421 | B2 | 1/2006 | Ikeda et al. | |
| 7,055,378 | B2 | 6/2006 | Su et al. | |
| 7,083,270 | B2 | 8/2006 | Torii et al. | |
| 7,084,554 | B2 | 8/2006 | Xu et al. | |
| 7,104,134 | B2 | 9/2006 | Amano et al. | |
| 7,195,909 | B2 | 3/2007 | Klenerman et al. | |
| 7,263,874 | B2 | 9/2007 | Fitch et al. | |
| 7,497,133 | B2 | 3/2009 | Shih et al. | |
| 2002/0094528 | A1 | 7/2002 | Salafsky | |
| 2002/0117659 | A1 | 8/2002 | Lieber et al. | |
| 2002/0155303 | A1 | 10/2002 | Wielstra et al. | |
| 2003/0032293 | A1 | 2/2003 | Kim et al. | |
| 2003/0068655 | A1 | 4/2003 | Bottomley et al. | |
| 2003/0194697 | A1 | 10/2003 | Klenerman et al. | |
| 2003/0224551 | A1 | 12/2003 | Kim et al. | |
| 2003/0235681 | A1 | 12/2003 | Sebastian et al. | |
| 2004/0022677 | A1 | 2/2004 | Wohlstadter et al. | |
| 2004/0265664 | A1 | 12/2004 | Badding et al. | |
| 2005/0112621 | A1 | 5/2005 | Kim et al. | |
| 2005/0114045 | A1 | 5/2005 | Giurgiutiu et al. | |
| 2005/0199047 | A1 | 9/2005 | Adams et al. | |
| 2005/0277852 | A1 | 12/2005 | Shih et al. | |
| 2005/0287680 | A1 | 12/2005 | Venkatasubbarao et al. | |
| 2006/0053870 | A1 | 3/2006 | Berndt | |
| 2006/0217893 | A1 | 9/2006 | Li et al. | |
| 2006/0228657 | A1 | 10/2006 | Masters et al. | |
| 2006/0257286 | A1 * | 11/2006 | Adams | 422/82.01 |
| 2007/0089515 | A1 | 4/2007 | Shih et al. | |
| 2007/0141721 | A1 | 6/2007 | Vafai et al. | |
| 2007/0169553 | A1 | 7/2007 | Mutharasan | |
| 2007/0183190 | A1 * | 8/2007 | Eyckmans et al. | 365/173 |
| 2007/0218534 | A1 | 9/2007 | Klenerman et al. | |
| 2008/0034840 | A1 | 2/2008 | Mutharasan | |
| 2008/0035180 | A1 | 2/2008 | Mutharasan | |
| 2009/0053709 | A1 | 2/2009 | Mutharasan | |
| 2009/0078023 | A1 | 3/2009 | Mutharasan | |
| 2009/0203000 | A1 | 8/2009 | Mutharasan | |

FOREIGN PATENT DOCUMENTS

| | | | |
|---|---|---|---|
| WO | 98/50773 | A2 | 11/1998 |
| WO | 2004/061991 | A1 | 7/2004 |
| WO | 2005/043126 | A2 | 5/2005 |
| WO | 2006/031072 | A1 | 3/2006 |
| WO | WO2006039506 | A2 | 4/2006 |
| WO | 2007/087328 | A2 | 8/2007 |
| WO | 2007/133619 | A1 | 11/2007 |
| WO | 2008/020903 | A2 | 2/2008 |
| WO | 2008/021187 | A2 | 2/2008 |
| WO | 2008/021189 | A2 | 2/2008 |
| WO | 2008/101199 | A1 | 8/2008 |
| WO | 2009/014830 | A1 | 1/2009 |
| WO | 2009/035732 | A2 | 3/2009 |
| WO | 2009/035732 | A3 | 3/2009 |

OTHER PUBLICATIONS

Weng, L. et al., "Effect of acetylacetone on the preparation of PZT materials in sol/gel processing", Mater. Sci. Engin., B96: 307-312 (2002).
Wilson, L S et al., "Elastography—the movement begins", Phys. Med. Biol., 45: 1409-1421 (2000).
Wilson, L., et al., "Pezoelectric-excited millimeter-sized cantilever (PEMC) sensor provides viscosity and density measurements," Submitted to Review of Scientific Instruments, 1-26, Jan. 19, 2010.
Yi, J. W. et al., "Effect of length, width, and mode on the mass detection sensitivity of piezoelectric unimorph cantilevers", J. Appl. Phys., 91(3): 1680-1686 (2002).
Yi, J. W. et al., "In situ cell detection using piezoelectric lead zirconate titanate-stainless steel cantilevers", J. Appl. Phys., 93(1): 619-625 (2003).
Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.
Zhou, J. et al., "Zeolite-modified microcantilever gas sensor for indoor air quality control," Sensors and Actuators B, Oct. 1, 2003, 94(3), 337-342.
Zhu, D.M. et al., "Thermal conductivity and electromechanical property of single-crystal lead magnesium niobate titanate", Appl. Phys. Lett., 75(24): 3868-3870 (1999).
Data of Commercially Available Product, EDO Corporation: 1-8 (1999).
Data of Commercially Available Product, APC International, Ltd.: 1-2 (2005).
Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).
Campbell, G.A., et al., "Method of measuring *Bacillus anthracis* spores in the Presence of copious amounts of *Bacillus thurigiensis* and *Bacillus cereus*," Anal. Chem. 79, 1145-1152 (2007).
Campbell, G.A., et al., "PEMC sensor's mass change sensitivity is 20 pg/Hz under liquid immersion," Biosensors and Bioelectronics, 22, 35-41 (2006).
Campbell, G.A., et al., "Detection of *Bacillus anthracis* spores and a model protein usings PEMC sensors in a flow cell at 1 mL/min," Biosensors and Bioelectronics, 22, 78-85 (2006).
Campbell, G.A., et al., "Detection of airborne *Bacillus anthracis* spores by an integrated system of an air sampler and a cantilever immunosensor," Sensors and Actuators B 127, 376-382 (2007).
Maraldo, et al., "Method for Label-Free Detection of Femtogram Quantities of Biologics in Flowing Liquid Samples," Anal. Chem. 79, 2762-2770 (2007).
Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).

Rijal, et al., "PEMC-based method of measuring DNA hybridization at femtomolar concentration directly in human serum and in the presence of copious noncomplementary strands," Anal. Chem., 79, 7392-7400 (2007).
Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb2/3)O3-0.1PbTiO3 and Pb(Mg1/3Nb2/3) O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Li, et al., Micromachined Biomimetic Sensor Using a Modular Artificial Hair Cells, pp. 1-3, Jan. 19, 2010.
Thaysen, "Label. free Detection, BioMEMs Materials and Fabrication Methods," Track 2, 3:00pm, pp. 1-3, Sep. 7, 2002.
Hwang, II-Han et al., "Self-actuating biosensor using a piezoelectric cantilever and its optimization": In International MEMS Conference 2006, Journal of Physics: Conference Series 34. May 2006, pp. 362-367.
Kanda, T. et al., "A flat type touch probe sensor using PZT thin film vibrator", Sensors and Actuators 83. 2000, pp. 67-75.
Kim, Sang-Jin et al., "Fabrication and Characterization of Pb(Zr,Ti)O3 Microcantilever for Resonance Sensors", Jpn. J. Appl. Phys., vol. 42. Mar. 2003, pp. 1475-1478.
Lee, Chengkuo et al., "Self-excited piezoelectric PZT microcantilevers for dynamic SFM—with inherent sensing and actuating capabilities", Sensors and Actuators A 72. 1999, pp. 179-188.
Lee, Jeong Hoon et al., "Immunoassay of prostate-specific antigen (PSA) using resonant frequency shift of piezoelectric nanomechanical microcantilever", Biosensors and Bioelectronics Apr. 20, 2005. pp. 2157-2162.
Lee, Seung S. et al., "Self-excited Piezoelectric Cantilever Oscillators": In the 8th International Conference on Solid-State Sensors and Actuators, and Eurosensors IX. Jun. 1995, pp. 417-420.
Lee, Yeolho et al., "A Piezoelectric Micro-Cantilever Bio-Sensor Using the Mass-Microbalancing Technique With Self-Excitation": In the 13th International Conference on Solid-State Sensors, Actuators and Microsystems. Jun. 2005, pp. 644-647.
Pons, Thomas et al., "Solution-phase single quantum dot fluorescence resonance energy transfer", J. American Chemical Society, vol. 128, No. 47. 2006, pp. 15324-15331. Abstract only.
Shen, Zuyan et al., "Self-exciting, self-sensing PbZr0.53Ti0.47O3/SiO2 piezoelectric microcantilevers with femtogram/Hertz sensitivity", Applied Physics Letters 89. Jul. 2006, pp. 023506-1-023506-3.
Zhao, Qiang et al., "Array adsorbent-coated lead zirconate titanate (PZT)/stainless steel cantilevers for dimethyl methylphosphonate (DMMP) detection", Sensors and Actuators, vol. 117, No. 1. 2006, pp. 74-79. Abstract only.
Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).
Ammari, H. et al., "T-Scan Electrical Impedance Imaging System for Anomaly Detection", Siam J. Appl. Math., 65(1): 252-266 (2004).
Baselt, D. R. et al., "Biosensor based on force microscope technology", J. Vac. Sci. Technol. B, 14(2): 789-793 (1996).
Birnie, III, D. P. et al., "Coating uniformity and device applicability of spin coated sol-gel PXT films", Microelectronic Engineering, 29: 189-192 (1995).
Bondoux, C. et al., "MgO insulating films prepared by sol-gel route for SiC substrate", J. Europe. Ceramic Soc., 25: 2795-2798 (2005).
Brito, R. et al., "Adsorption of 3-mercaptopropyltrimethoxysilane and 3-aminopropyltrimethoxysilane at platinum electrodes", J. Electroanalytical Chem., 520: 47-52 (2002).
Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39, Jan. 19, 2010.
Campbell, G.A., et al., "Detection and quantification of proteins using self-excited PZT-glass millimeter-sized cantilever," Biosensors and Bioelectronics, 26-36, Jan. 22, 2005.
Campbell, G.A., "Piezoelectric-excited millimeter-sized cantilever (PEMC) sensors detect *Bacillus anthracis* at 300 spores/mL," Biosensors and Bioelectronics, 37-45, Sep. 19, 2005.
Campbell, G.A., et al., "kinetics of *bacillus anthracis* spore binding to antibody functionalized PEMC sensors in presence of *bacillus thuringiensis* and *bacillus cereus*," J. Publications, Am. Chem. Soc. 25 pages, Feb. 1, 2006.
Campbell, G.A., et al., "*Escherichia coli* O157:H7 detection limit of millimeter-sized PZT cantilever sensors in 700 cells/mL," Analytical Sci., 11-13, Apr. 2005.
Campbell, G.A., et al., "Detection of pathogen *Escherichia coli* O157:H7 using self-excited PZT-glass microcantilevers," Biosensors and Boelectronics, 14-25, Jan. 2005.
Campbell, G.A., "Detection of *Staphylococcus enterotoxin* B at pictogram levels using piezoelectric-excited millimeter-sized cantilever sensors," Submitted on line to J. of Analytical Chem., 1-24, Mar. 29, 2006.
Capobianco, J. A., et al., "Methyltrimethoxysilane-insulated piezoelectric microcantilevers for direct, all-electrical biodetection in buffered aqueous solutions", Rev. Sci. Instrum., 77: 125105-1-125105-6 (2006).
Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).
Carlier, S. G., et al., "Elastography", J. Cardiovasc Risk, 9(5): 237-245 (2002).
Carr, D.W., et al., "Fabrication of nanoelectromechanical systems in single crystal silicon using silicon on insulator substrates and electron beam lithography," J. Vac. Sci. Technology, B, 5(6), 2760-2763, Dec. 1977.
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20 (20): 8762-8767 (2004).
Cho, S. H. et al., "Micro-scale metallization on flexible polyimide substrate by Cu electroplating using SU-8 photoresist mask", Thin Solid Films, 475: 68-71 (2005).
Duval, F.F.C. et al., "Stable TiO2/Pt electrode structure for lead containing ferroelectric thick films on silicon MEMS structures", Thin Solid Films, 444: 235-240 (2003).
Feili, D. et al., "Encapsulation of organic field effect transistors for flexible biomedical microimplants", Sensors and Actuators, A120: 101-109 (2005).
Ferrini, R. et al., "Screening Mammography for Breast Cancer: American College of Preventive Medicine Practice Policy Statement", www.acpm.org/breast, pp. 1-4 (2005).
Fritz, J. et al., "Translating Biomolecular Recognition into Nanomechanics", Science, 288: 316-318 (2000).
Fung, Y. S. et al., "Self-Assembled Monolayers as the Coating in a Quartz Piezoelectric Crystal Immunosensor to Detect Salmonella in Aqueous Solution", Anal. Chem., 73: 5302-5309 (2001).
Gao, L. et al., "Imaging of the elastic properties of tissue: A review", Ultrasound in Med. & Biol., 22(8): 959-977 (1996). Abstract Only.
Greenleaf, J. F. et al., "Selected Methods for Imaging Elastic Properties of Biological Tissues", Annu. Rev. Biomed. Eng., 5: 57-78 (2003).
Gu, H. et al., "Single-Calcination Synthesis of Pyrochlore-Free 0.9Pb(Mg1/3Nb2/3)O3-0.1PbTiO3 and Pb(Mg1/3Nb2/3)O3 Ceramics Using a Coating Method", J. Am. Ceram. Soc., 86(2): 217-221 (2003).
Haccart, T. et al., "Evaluation of niobium effects on the longitudinal piezoelectric coeffecients of Pb(Zr,Ti)O3 thin films", Appl. Phys. Lett., 76(22): 3292-3294 (2000).

Han, W. et al., "A magnetically driven oscillating probe microscope for operations in liquids", Appl. Phys. Lett., 69(26): 4111-4113 (1996).
Hiboux, S. et al., "Mixed titania-lead oxide seed layers for PZT growth on Pt(111): a study on nucleation, texture and properties", J. Europe. Ceram. Soc., 24: 1593-1596 (2004).
Hwang, I.H. et al., "Self-actuating biosensor using a piezoelectric cantilever and its optimization", Journal of Physics: Conference Series 34, pp. 362-367, 2006.
Hwang, K.S. et al., "In-situ quantitative analysis of a prostate-specific antigen (PSA) using a nanomechanical PZT cantilever", Lab Chip, 4: 547-552 (2004).
Ilic, B. et al., "Mechanical resonant immunospecific biological detector", Appl. Phys. Lett., 77(3): 450-452 (2000).
Itoh, T. et al., "Self-excited force-sensing microcantilevers with piezoelectric thin films for dynamic scanning force microscopy", Sensor and Actuators, A54:477-481 (1996).
Jung, S.K. et al., "Polymeric Mercaptosilane-Modified Platinum Electrodes for Elimination of Interferants in Glucose Biosensors", Anal. Chem., 68: 591-596 (1996).
Kanda, T. et al., "A flat type touch probe sensor using PZT thin film vibrator", Sensors and Actuators, 83: 67-75 (2000).
Katiyar, P. et al. "Electrical properties of amorphous aluminum oxide thin films", Acta Materialia, 53: 2617-2622 (2005).
Keller, A. et al., "Reliability of Computed Tomography Measurements of Paraspinal Muscle Cross-Sectional Area and Density in Patients With Chronic Low Back Pain", Spine, 28(13): 1455-1460 (2003).
Kelly, J. et al., "Effect of Composition on the Electromechanical Properties of (1-x)Pb(Mg1/3Nb2/3)O3-xPbTiO3 Ceramics" J. Am. Ceram. Soc., 80(4): 957-964 (1997).
Khabari, A. et al., "Partially ionized beam deposition of parylene" J. Non-Crystalline Solids, 351: 3536-3541 (2005).
Kim, S.H. et al., "Influence of A12O3 diffusion barrier and PbTiO3 seed layer on microstructural and ferroelectric charachteristics of PZT thin films by sol-gel spin coating method," Thin Solid Films, 305: 321-326 (1997).
Kim, S.J. et al., "Fabrication and Characterization of Pb(Zr,Ti)O3 Microcantilever for Resonance Sensors," Jpn. J. Appl. Phys., 42(3): 1475-1478 (2003).
Klissurska, R.D. et al. "Microstructure of PZT sol-gel films on Pt substrates with different adhesion layers," Microelectronic Engineering, 29: 297-300 (1995).
Kruse, S.A. et al., "Tissue characterization using magnetic resonance elastography: preliminary results," Phys. Med. Biol., 45: 1579-1590 (2000).
Kumar, V. et al., "A Simple System for the Preparation of Submicrometer Lead Titanate Powders by the Sol-Gel Method," J. Am. Ceram. Soc., 79(10): 2775-2778 (1996).
Kwok, CLK. et al., "Low temperature perovskite formation of lead zirconate titanate thin films by a seeding process," J. Mater. Res., 8(2): 339-344 (1993).
Lee, C. et al., "Sol-gel derived PZT force sensor for scanning force microscopy", Mater. Chem. Phys., 44: 25-29 (1996).
Lee, C. et al., "Self-excited piezoelectric PZT microcantilevers for dynamic SFM—with inherent sensing and actuating capabilities", Sensors and Actuators, A72: 179-188 (1999).
Lee, J. H. et al., "Label free novel electrical detection using micromachined PZT monolithic thin film cantilever for the detection of C-reactive protein", Biosensors and Bioelectronics, 20: 269-275 (2004).
Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).
Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).
Lee, S. S. et al., "Self-Excited Piezoelectric Cantilever Oscillators", The 8th International Conference on Solid-State Sensors and Actuators, and Eurosensors IX, Stockholm, Sweden: 417-420 (1995).
Lee, Y. et al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).
Li, S. et al., "The intrinsic nature of nonlinear behavior observed in lead zirconate titanate ferroelectric ceramic", J. Appl. Phys., 69(10): 7219-7224 (1991).
Li, X. et al., "Detection of water-ice transition using a lead zirconate titanate/brass transducer", J. Appl. Phys., 92(1): 106-111 (2002).
Lin, Z. et al., "Operation of an Ultrasensitive 30-MHz Quartz Crystal Microbalance in Liquids", Anal. Chem., 65(11): 1546-1551 (1993).
Liu, W. et al., "Preparation and orientation control of Pb1.1(Zr0.3Ti0.7)O3 thin films by a modified sol-gel process", Mat. Lett., 46: 239-243 (2000).
Luo, H. et al., "Synthesis of PMN and 65PMN-35PT Ceramics and Films by a New Suspension Method", Perovskite, Piezoelectric, and Dielectric Ceramics: 251-260, Jan. 3, 2006.
Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).
Luo, H., "Colloidal Processing of PMN-PT Thick Films for Piezoelectric Sensor Applications", A Thesis Submitted to the Faculty of Drexel University in Jun. 2005.
Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).
Maraldo, D. et al., "Resonant-mode millimeter sized cantilever biosensor for continuous detection of proteins and pathogens in flowing liquids," Dept. of Chem. and Biological Eng., 1-21, May 15, 2006.
Matsui, Y. et al., "Highly Oxidation-Resistant TiN Barrier Layers for Ferroelectric Capacitors", Jpn. J. Appl. Phys., 36 (3B): 1586-1588 (1997).
Mazza, E. et al., Biomechanics, http://www.zfm.ethz.ch/e/res/bio/, 1-10, Sep. 28, 2004.
McGovern, J.P. et al., "Real-Time Salmonella Detection Using Lead Zirconate Titanate-Titanium Microcantilevers", Mater. Res. Soc. Symp. Proc., 845: AA3.8.1-AA3.8.6 (2005).
Mueller, V. et al., "Nonlinearity and scaling behavior in donor-doped lead zirconate titanate piezoceramic", Appl. Phys. Lett., 72(21): 2692-2694 (1998).
Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).
Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).
Nguyen, L. T. T. et al., "Synthesis and characterization of a photosensitive polyimide precursor and its photocuring behavior for lithography applications", Optical Materials, 29: 610-618 (2007).
Oden, P. I. et al., "Viscous drag measurements utilizing microfabricated cantilevers", Appl. Phys. Lett., 68(26): 3814-3816 (1996).
Ohnmacht, M. et al., "Microcoils and microrelays—an optimized multilayer fabrication process", Sensors and Actuators, 83: 124-129 (2000).
Park, G.T. et al., "Measurement of piezoelectric coefficients of lead zirconate titanate thin films by strain-monitoring pneumatic loading method", Appl. Phys. Lett., 80(24): 4606-4608 (2002).
Park, S.E. et al., "Ultrahigh strain and piezoelectric behavior in relaxor based ferroelectric single crystals", J. Appl. Phys., 82(4): 1804-1811 (1997).
Piezo Systems, Inc., "Piezoceraminc Sheets and Their Properties", Piezo Systems, Inc. Catalog: 1-3 (2007).
Pons, T. et al., "Solution-phase single quantum dot fluorescence resonance energy transfer", J. Amer. Chem. Soc., 128(47): 15324-15331 (2006). Abstract Only.
Ren, W. et al, "Non linear strain and DC bias induced piezoelectric behaviour of electrostrictive lead magnesium niobate-lead titanate ceramics under high electric fields", J. Phys. D: Appl. Phys., 35: 1550-1554 (2002).

Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).
Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).
Shih, W. et al., "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).
Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl. Phys. Lett., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Ward, M. D. et al., "In Situ Interfacial Mass Detection with Piezoelectric Transducers", Science, 249: 1000-1007 (1990).
Wellman, P. S. et al., "Breast Tissue Stiffness in Compression is Correlated to Histological Diagnosis", http://biorobotics.harvard.edu/pubs/mechprops: 1-15, Jan. 19, 2010.
Wellman, P. S. et al., "Tactile Imaging of Breast Masses", Arch. Surg., 136: 204-208 (2001).
Auge, J. et al.: "High-Speed Multi-Parameter Data Acquisition and Web-Based Remote Access to Resonant Sensors an Sensor Arrays," vol. 95, Nos. 1-3, Oct. 15, 2003, Elsevier S.A, Switzerland, pp. 32-38, XP004454645.
European Search Report; Mailed Jan. 7, 2013 for corresponding EP Application No. 08782746.5.

* cited by examiner

HAND-HELD PHASE-SHIFT DETECTOR FOR SENSOR APPLICATIONS

STATEMENT OF GOVERNMENT INTEREST

This invention was reduced to practice with Government support under Grant No. R01 EB000720 awarded by the National Institutes of Health and Grant No. CHE-0442100 awarded by the National Science Foundation; the Government is therefore entitled to certain rights to this invention.

BACKGROUND OF THE INVENTION

1. Field of the Invention

The invention relates to a portable hand-held phase-shift detector capable of interfacing with piezoelectric microcantilever sensors (PEMS) and methods for using the detector and a system including the detector. The invention is particularly useful as a sensor or diagnostic device.

2. Description of the Related Technology

Biosensors and chemical sensors coupled with impedance analyzers are well known in the art. For example, U.S. Pat. No. 6,278,379 and U.S. publication nos. 20060257286 and 20060217893 discloses sensor systems incorporating an impedance analyzer to detect changes in resonance frequency.

Current impedance analyzers, however, are typically bulky, heavy and relatively immobile, thereby limiting the circumstances in which resonance frequency may be measured. Although some impedance analyzers, such as impedance analyzers for determining the physical properties of large structures such as a building and impedance analyzers for determining body composition have been made portable, as disclosed by U.S. patent application publication no. 2005/0114045 and U.S. Pat. No. 6,280,396, impedance analyzers for use with chemical sensors or biosensors remain large, cumbersome and relatively immobile.

Therefore there is a need to develop a light, portable, hand-held detector to facilitate diagnostic or sensor applications.

SUMMARY OF THE INVENTION

The invention is directed to a novel phase-shift detector capable of interfacing with an array of sensors.

In one aspect of the invention, the phase-shift detector is lightweight and portable.

In another invention, the phase-shift detector is a hand-held device capable of fitting within the palm of a hand.

BRIEF DESCRIPTION OF THE DRAWINGS

FIG. 1(*b*) is a photograph of the hand-held phase shift detector interfaced with an array of detectors for *Bacillus anthracis* spores.

FIG. 2(*b*) is a photograph of a hand-held, portable phase-shift detector

FIG. 2(*c*) an optical micrograph of an array of four lead-magnesium niobate-lead titanate solid solution (PMN-PT)/Cu PEMS.

FIG. 4(*b*) is a graph of resonance frequency versus time showing the simultaneous detection of three PEMS, one coated with scFv of HER2, one coated with PSA antibodies and one coated with gp120 antibodies in an 18 μg/ml PSA solution.

FIG. 4(*c*) is a graph of resonance frequency versus time showing the simultaneous detection of three PEMS, one coated with scFv of HER2, one coated with PSA antibodies and one coated with gp120 antibodies in a 100 μg/ml gp120 solution.

DETAILED DESCRIPTION OF THE PREFERRED EMBODIMENTS

Figure 1A:
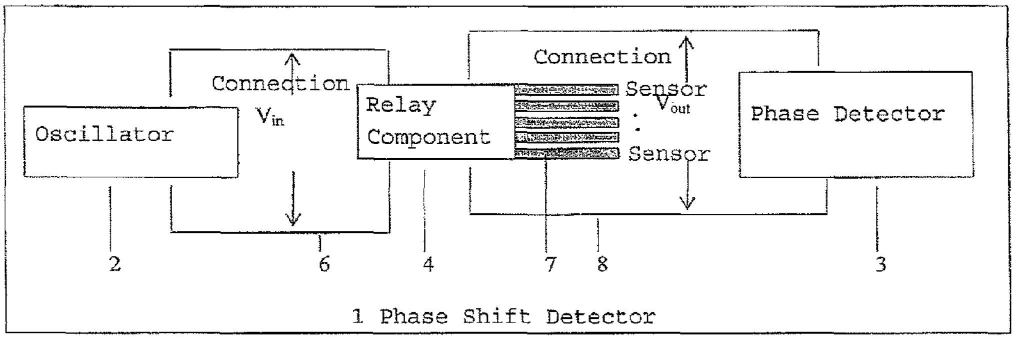
FIG. 1(*a*) is a schematic of the hand-held phase detector, oscillator, phase detector and relay component.
Figure 1B:
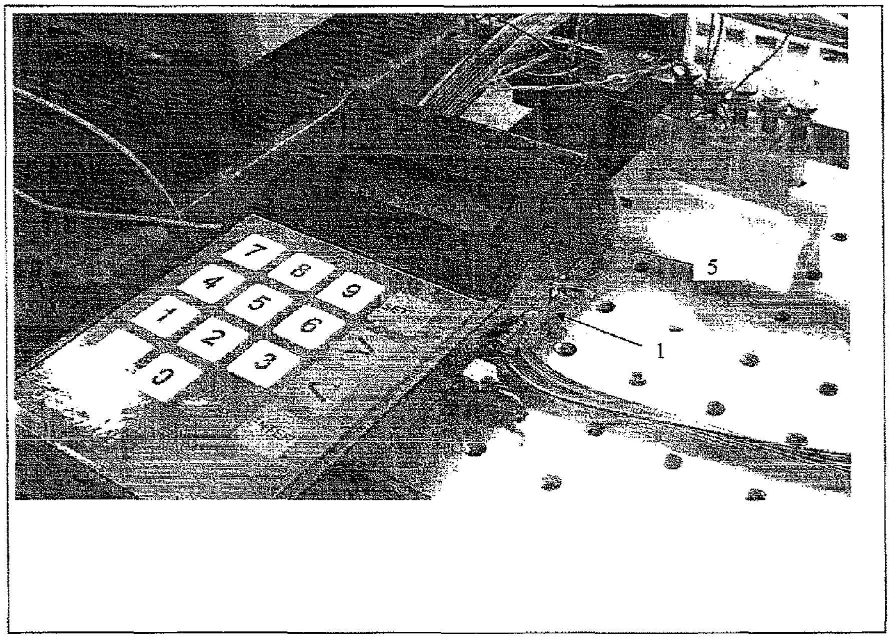

The invention is directed to a portable hand-held phase-shift detector 1, capable of simultaneously interfacing with and monitoring one or more sensors 7, as shown in FIGS. 1(*a*) and 1(*b*). Phase-shift detector 1 comprises an oscillator 2, a phase detector 3, a relay component 4 and a display screen 5. The relay component 4 rotates the connection of phase detector 3 and oscillator 2 among the connected sensors 7 in the sensor array to enable phase detector 3 to measure the output of each sensor 7.

Oscillator 2 comprises a resonance circuit, including a transmission line, a circuit substrate, chip components mounted on the circuit substrate, and an amplifying circuit for amplifying a resonance signal generated by the resonance circuit. Connected to sensors 7 by a connection 6, oscillator 2 generates an input signal or voltage to actuate sensors 7. Oscillator 2 preferably actuates sensors 7 by inducing oscillation of sensors 7 in a frequency range that encompasses the resonance frequencies of sensors 7 to enable detection of resonance frequency shift of sensors 7 resulting from analyte binding.

Phase detector 3 measures the magnitude and phase shift of the output voltage of sensors 7 through a connection 8. A maximum in the phase shift plotted versus frequency identifies the resonance frequency. A significant shift in resonance frequency indicates the binding of a particular compound or molecule to the specific receptor on a sensor surface, and thereby, verifies the presence of said compound or molecule in the environment being tested.

In one embodiment, oscillator 2 may be a microprocessor-controlled signal generator. Phase-shift detector 1 may optionally include a display screen 5 for displaying results in any suitable manner such as in a numerical or graphical format. In a preferred embodiment, phase-shift detector 1 may also include a data transmitter for transmitting data to an electronic information storage medium such as a computer or computer disk. Display screen 5, or other suitable means, may function as an indicator which provides an indication of the presence of a specific analyte. Alternatively, display screen 5 or other suitable means may function as an indicator which provides an indication if a specific analyte is present in an amount which exceeds a threshold value.

As shown in FIG. 1(*b*), portable hand-held phase-shift detector 1 may be incorporated in, or work in conjunction with, any suitable sensor system. In a preferred embodiment, phase-shift detector 1 is associated with one or more piezoelectric microcantilevers (PEMS) or piezoelectric microdisks and enables detection of the magnitude and phase shift of an output voltage of each PEMS. Phase-shift detector 1 may be powered by any standard power source. In a preferred embodiment, the power source is portable, small and lightweight, such as a typical 9 volt battery. Hand-held phase-shift detector unit 1 may be about 3.5 inches by 7.5 inches in size. Preferably, phase-shift detector unit 1 may be simultaneously connected to a plurality of sensors. In a preferred embodiment, phase-shift detector unit 1 is simultaneously connected to from about eight sensors to about thirty-two sensors. Preferably, the entire system is sufficiently small to be carried by a single person to a site of detection.

In a preferred embodiment, the hand-held phase shift detector 1 has dimensions of up to about 7.5 cm deep by about 30 cm high by about 30 cm wide and weight of no more than about 2 kg and may simultaneously operate as many as 32 sensors. The array sensors and their holder may be no larger than about 2 cm in width, about 2 cm in depth, and about 1 cm in height and weigh no more than 50 g. The phase-shift detector 1 may further include a relay mechanism, such as a ribbon cable, for facilitating connection 6 and connection 8. Preferably, the ribbon cable is less than 1 m long, less than 3 cm wide, and weighs less than 50 g. Preferably, the total weight of the system including hand held phase shift detector 1 and sensors 7 is not more than 2.5 kg.

Advantageously small, the device is both portable and robust. In a preferred embodiment, the device may fit within the palm of a hand. Since the phase-shift detector is simple in design, it may be easily and inexpensively manufactured and may be made available as an off-the-shelf product for numerous applications. The phase-shift detector may be used in biosensor, diagnostics or any molecular or chemical sensor applications.

EXAMPLES

Example 1

Figures 2A, 2B, 2C:
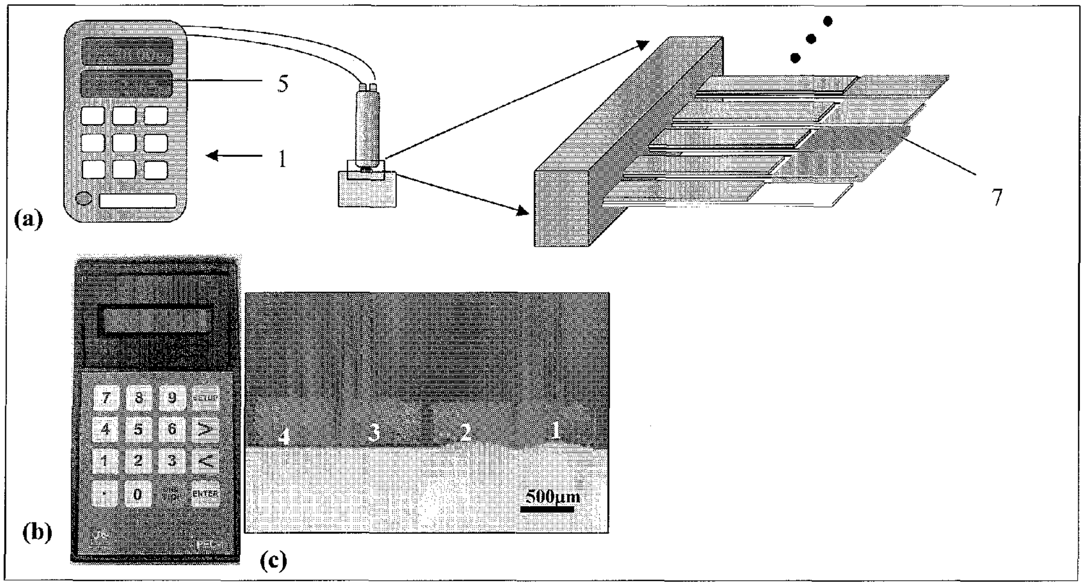
FIG. 2(*a*) is a schematic of a hand-held phase-shift detector working with an array of PEMS capable of simultaneous detection of multiple antigens.

FIG. 2(*b*) shows one embodiment of a phase-shift detector, comprising an Analog Devices AD8203 RF gain/phase detector IC as the measuring device and an Analog Devices AD9850 DDS Frequency Synthesizer as a high resolution microprocessor-controlled signal generator, in combination with an array of PEMS. The phase-shift detector of FIG. 2(*a*) is capable of monitoring at least 8 PEMS at the same time.

Example 2

Figure 3:
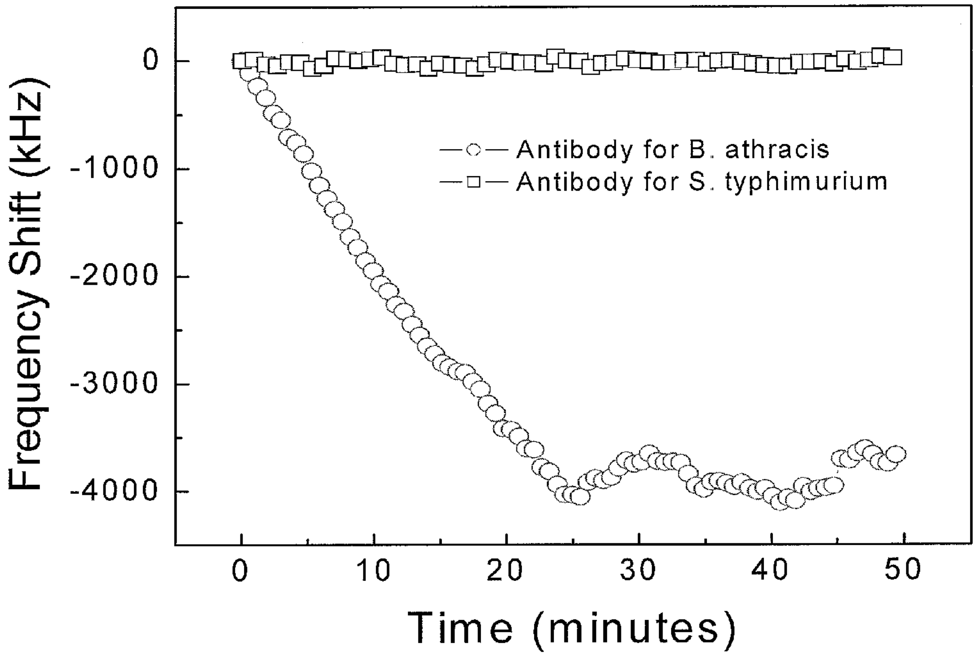
FIG. 3 is a graph of resonance frequency shift versus time showing the detection of *Bacillus anthracis* spores using a hand held phase-shift detector.

FIG. 1(*b*) shows a phase-shift detector and an array of PEMS. The hand-held phase shift-detector accurately detected the frequency shift of each PEMS. FIG. 3 shows the results of an experimental study for detecting *Bacillus anthracis* (BA) processed with the phase-shift detector of FIG. 1(*b*). The open circles represent PZT/glass PEMS with a 2 mm long glass tip coated with antibody specific to BA spores, and the open squares represent cantilevers coated with antibody specific to *S. typhimurium* and not specific to BA spores. The phase-shift detector accurately reported that the PEMS identified the presence of BA spores from only the PEMS coated with antibodies specific to BA spores; by comparison, the PEMS coated with antibodies specific to *Salmonella* did not detect the BA spores. The results therefore demonstrate that the hand-held phase-shift detector is capable of generating accurate results similar to those obtained by an impedance analyzer.

Example 3

A hand-held phase-shift detector in combination with an array of 3 PEMS was used to detect the presence of various antigens. Each PEMS had a different receptor immobilized on its surface including, anti-gp120, anti-PSA, and scFv of Her2. gp120 is a surface protein on human immunodeficiency viruses (HIV). PSA (prostate specific antigen) is a prostate cancer marker, and HER2 is a member of the epidermal growth factor receptor linked to breast cancer and other cancers and scFv is an engineered single-chain variable fragment receptor.

Figure 4:
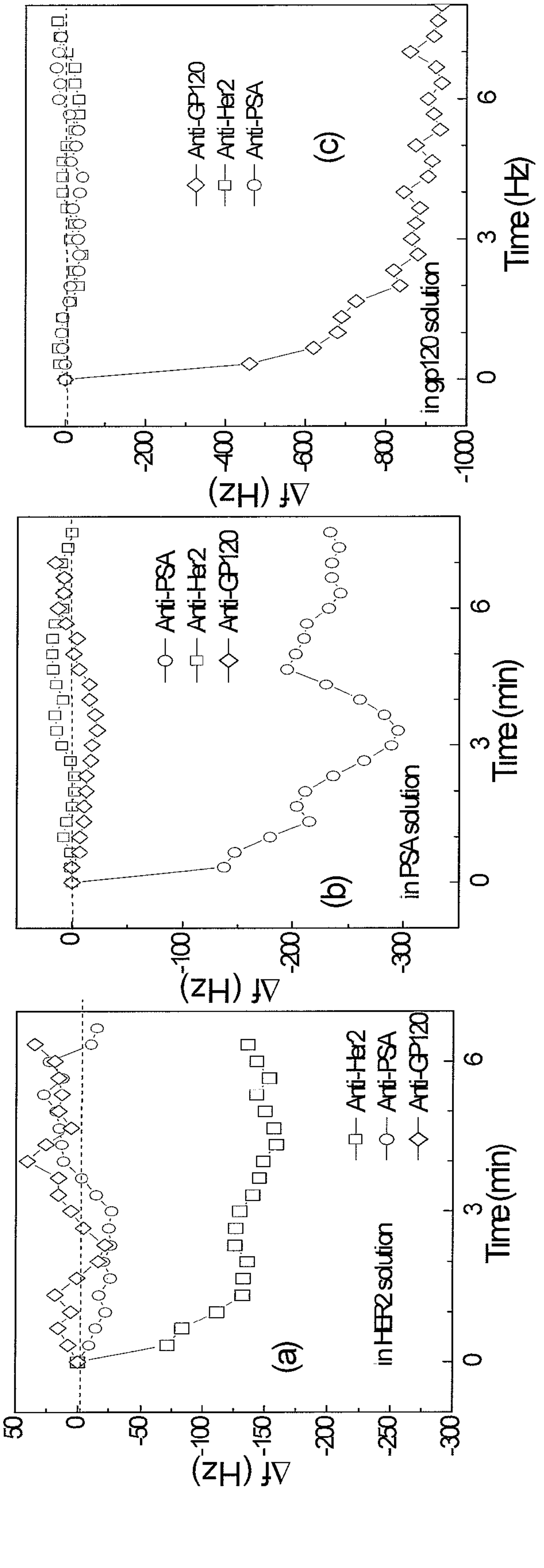
FIG. 4(*a*) is a graph of resonance frequency versus time showing the simultaneous detection of three PEMS, one coated with scFv of HER2, one coated with PSA antibodies and one coated with gp120 antibodies in a 23 μg/ml HER2 solution.

The PEMS were placed in 3 different solutions, each containing an antigen specific to each receptor. As shown in FIG. 4, the phase-shift detector correctly reported that only the PEMS having the antigen specific receptor corresponding to the marker present in the solution responded when the array was submerged in each solution. FIG. 4(*a*) shows that only the PEMS with scFv to HER2 responded to HER2. FIG. 4(*b*) shows that only the PEMS with antibodies to PSA responded to PSA, and FIG. 4(*c*) shows that only the PEMS with antibodies to gp120 responded to gp120. This experiment clearly illustrates that the phase-shift detector and PEMS array are capable of simultaneously detecting multiple antigens.

Example 4

Figure 5:
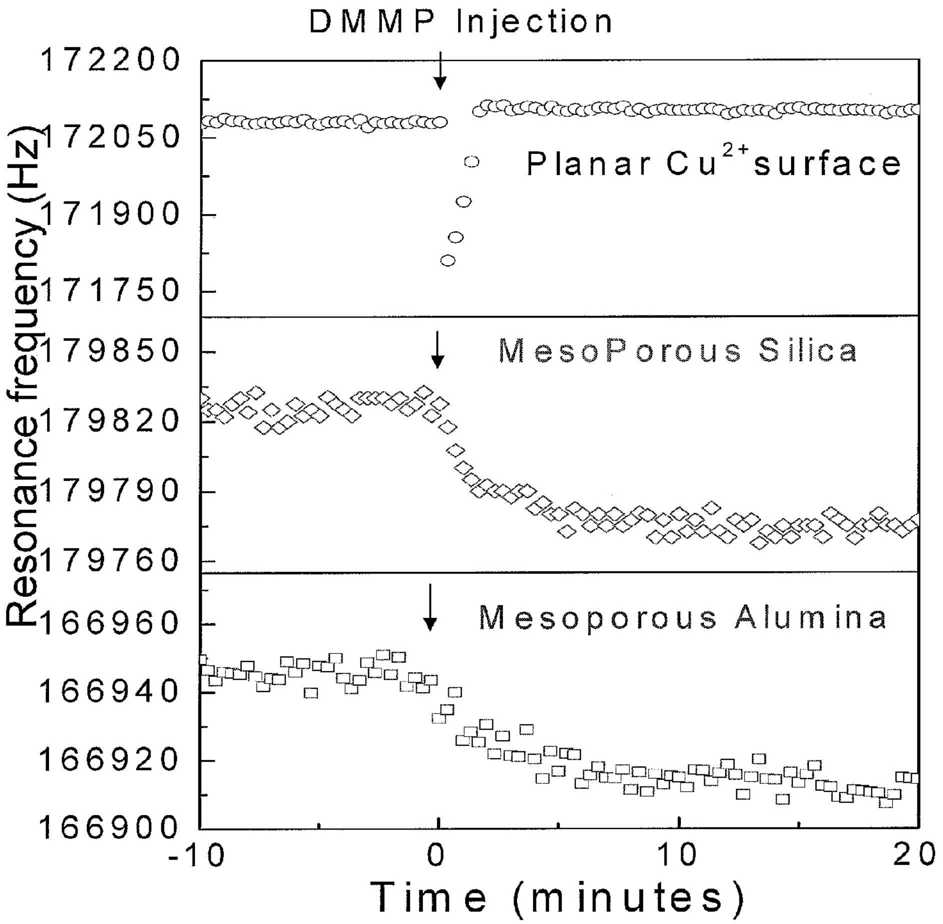
FIG. 5 is a graph of resonance frequency versus time showing a unique DMMP detection pattern.

The hand-held phase-shift detector, in combination with a PEMS array, may also be used to detect gases/chemicals. Unlike biological detection where antibody-antigen binding is specific, most receptors for gas/chemical detection are not selective. By using a PEMS array having different receptors, it is possible to create a customized detection pattern for a gas or chemical. The custom combination of the PEMS array increases detection sensitivity and the accuracy of chemical or gas detection. FIG. 5 shows a unique PEMS array for dimethyl methylphosphonate (DMMP), a nerve gas simulant.

Three lead magnesium niobate-lead titanate solid solution (PMN-PT)/Cu PEMS are each coated with a different receptor which is immobilized on the PEMS surface by microporous silica, mesoporous alumina and a monolayer of $Cu^{2+}$ ions on a self-assembled monolayer of 11-mercaptoundecanoic acid (MUA) to detect DMMP.

Having described the preferred embodiments of the invention which are intended to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, the intended scope of protection is set forth in the appended claims.

The invention claimed is:

1. A portable device for detecting a phase shift comprising:

an oscillator for generating an input signal at a desired frequency, a connection to said oscillator capable of providing an operative connection of said oscillator to at least one sensor to induce oscillation of said sensor, and a phase detector capable of detecting a phase shift between an initial output voltage from said at least one sensor induced by said oscillation of said sensor prior to exposure to a sample and an output voltage from said at least one sensor induced by said oscillation upon exposure of said at least one sensor to the sample.

2. The device of claim 1, wherein the device is capable of being operatively connected to an array of multiple sensors.

3. The device of claim 2, further comprising a relay for selectively connecting said phase detector to each of said sensors for selective receipt of the output voltage from that sensor.

4. The device of claim 1, wherein the oscillator is a microprocessor controlled signal generator.

5. The device of claim 3, wherein the sensors are selected from the group consisting of:

piezoelectric microcantilevers and piezoelectric microdisks.

6. The device of claim 1, wherein the phase detector is an RF gain/phase detector.

7. The device of claim 1, wherein the total weight of the device is not more than about 2 kg.

8. The device of claim 1, wherein the device has a size of not more than about 7.5 cm in depth, by 30 cm in width and 30 cm in height.

9. The device of claim 1, further comprising an indicator that generates an indication of the presence of an analyte.

10. The device of claim 1, further comprising an indicator that generates an indication of the presence of an amount of an analyte that exceeds a threshold amount.

11. A portable system for detecting the presence of an analyte comprising:

an oscillator for generating an input signal at a desired frequency, at least one sensor capable of generating an initial output voltage when provided with an input signal, a connection from said oscillator to said at least one sensor for providing said input signal to said sensor from said oscillator to induce oscillation of said sensor, a phase detector capable of detecting a phase shift between the initial output voltage from said at least one sensor induced by said oscillation of said sensor prior to exposure to a sample and an output voltage from said at least one sensor induced by said oscillation upon exposure of said at least one sensor to the sample, and a connection from said sensor to said detector for providing said voltage signal from said sensor to said detector, wherein said system is sufficiently small to be carried by a single person to a site of detection.

12. The system of claim 11, comprising multiple sensors, a connection from said oscillator to each sensor and a connection from each sensor to said detector.

13. The system of claim 12, further comprising a relay for selectively connecting said detector to each of said sensors for selective receipt of the output voltage from that sensor.

14. The system of claim 13, wherein the sensors are piezoelectric microcantilevers.

15. The system of claim 11, wherein the oscillator is a microprocessor controlled signal generator.

16. The system of claim 11, wherein the phase detector is an RF gain/phase detector.

17. The system of claim 11, wherein the total weight of the system is not more than about 2.5 kg.

18. The system of claim 11, wherein the system has a size of not more than about 7.5 cm in depth, by 30 cm in width and 30 cm in height.

19. The system of claim 11, further comprising an indicator that generates an indication of the presence of an analyte.

20. The system of claim 11, further comprising an indicator that generates an indication of the presence of an amount of an analyte that exceeds a threshold amount.

* * * * *

UNITED STATES PATENT AND TRADEMARK OFFICE

CERTIFICATE OF CORRECTION

PATENT NO. : 8,456,150 B2
APPLICATION NO. : 12/524876
DATED : June 4, 2013
INVENTOR(S) : Shih et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 489 days.

Signed and Sealed this
Eighth Day of September, 2015

Michelle K. Lee
*Director of the United States Patent and Trademark Office*